United States Patent [19]
Biedermann et al.

[11] Patent Number: 6,150,403
[45] Date of Patent: *Nov. 21, 2000

[54] TOPICAL COMPOSITIONS FOR REGULATING THE OILY/SHINY APPEARANCE OF SKIN

[75] Inventors: Kimberly A. Biedermann, Cincinnati; Harry L. Schubert, Fairfield, both of Ohio; John J. Parran, Jr., Sebastian, Fla.

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 09/168,648

[22] Filed: Oct. 8, 1998

Related U.S. Application Data

[60] Provisional application No. 60/062,088, Oct. 14, 1997.

[51] Int. Cl.$^7$ ................................................ A61K 31/35
[52] U.S. Cl. ........................................................ 514/460
[58] Field of Search ........................... 424/7, 70, 401, 424/70.8, 402, 443; 514/852, 846, 944, 844, 106, 63, 460; 442/123

[56] References Cited

U.S. PATENT DOCUMENTS

| | | | |
|---|---|---|---|
| 4,062,939 | 12/1977 | Scott | 424/70 |
| 4,515,784 | 5/1985 | Bogardus et al. | 514/63 |
| 4,529,588 | 7/1985 | Smith et al. | 424/70 |
| 4,532,937 | 8/1985 | Miller | 128/759 |
| 4,548,973 | 10/1985 | Raynor | 524/102 |
| 4,643,939 | 2/1987 | Sugiyama et al. | 428/283 |
| 4,940,578 | 7/1990 | Yoshihara et al. | 424/70.8 |
| 5,053,222 | 10/1991 | Takasu et al. | 514/106 |
| 5,139,782 | 8/1992 | Jung | 424/401 |
| 5,344,651 | 9/1994 | Schwen et al. | 424/402 |
| 5,380,528 | 1/1995 | Alban et al. | 424/401 |
| 5,425,954 | 6/1995 | Thompson et al. | 424/401 |
| 5,587,176 | 12/1996 | Warren et al. | 424/443 |
| 5,833,998 | 11/1998 | Biedermann et al. | 424/401 |

FOREIGN PATENT DOCUMENTS

| | | | |
|---|---|---|---|
| 0 138 572 | 4/1985 | European Pat. Off. | C08B 37/08 |
| 282823 | 3/1988 | European Pat. Off. | A61K 7/48 |
| 0 308 919 A1 | 3/1989 | European Pat. Off. | A61K 7/42 |
| 396184 | 5/1996 | European Pat. Off. | A61K 31/00 |
| 335442 | 11/1996 | European Pat. Off. | A61K 31/495 |
| 2746108 | 9/1997 | France | C12G 1/02 |
| WO 92/09260 | 6/1992 | WIPO | A61K 7/16 |
| WO 95/26134 | 10/1995 | WIPO | A01N 25/32 |
| WO 96/00060 | 1/1996 | WIPO | A61K 31/195 |
| WO 97/17060 | 5/1997 | WIPO | A61K 7/48 |
| 9848774 | 5/1998 | WIPO | A61K 7/48 |

OTHER PUBLICATIONS

"Final Report on the Safety Assessment of Sodium Dehydroacetate and Dehydroacetic Acid", J. Amer. Coll. Toxicology, M. A. Liebert, Inc., Publisher, vol. 4, No. 3, pp. 123–159 (1985).

Ogo, K., et al., "Antibactericidal Effect of Kankohso 201 on Propionibacterium, a Normal Anaerobic Flora on Human Skin", Dept. of Microbiology, Okayama U. Med. School, pp. 59–64 (1981)—Translation.

Yoshimasa, H., et al., "The Sebum Lipid Assimilation and the Growth Inhibition of Pityrosporum Ovale", J. Soc. Cosmet. Chem. Japan, vol. 22, No. 3, pp. 165–170 (1988)—Translation.

*Primary Examiner*—William R. A. Jarvis
*Assistant Examiner*—Vickie Kim
*Attorney, Agent, or Firm*—Dara M. Kendall; Fumiko Tsuneki; Michael E. Hilton

[57] ABSTRACT

The present invention relates to methods for inhibiting sebaceous gland activity in mammalian skin comprising administration of a topical composition comprising dehydroacetic acid or pharmaceutically acceptable salts thereof, and a dermatologically-acceptable carrier. The present invention also relates to methods and topical compositions further comprising agents which regulate the oily and/or shiny appearance of skin, and agents which treat acne and related skin disorders in mammalian skin and scalp. Methods of reducing sebum synthesis with the use of dehydroacetic acid, methods of regulating the oily and/or shiny appearance of skin, and methods of treating acne and other skin disorders are also encompassed by the present invention.

3 Claims, No Drawings

TOPICAL COMPOSITIONS FOR REGULATING THE OILY/SHINY APPEARANCE OF SKIN

CROSS REFERENCE TO RELATED APPLICATION

This application claims the benefit of U.S. Provisional Application No. 60/062,088 filed Oct. 14, 1997.

TECHNICAL FIELD

The present invention relates to methods for inhibiting sebaceous gland activity in mammalian skin using dehydroacetic acid, or pharmaceutically acceptable salts thereof, in a dermatologically-acceptable carrier. The present invention also relates to methods and topical compositions further comprising agents which regulate the oily and/or shiny appearance of skin, and agents which treat acne and related skin disorders in mammalian skin and scalp.

BACKGROUND OF THE INVENTION

Sebum or skin oil is produced in the sebaceous glands located in the pilosebaceous apparatus of the skin and reaches the skin surface through ducts of the hair follicles. The presence of excessive amounts of sebum on the skin surface often results in an unattractive cosmetic condition commonly known as "oily skin." Depending on the regions of sebaceous gland activity and the level of sebum secretion, the population is often classified by skin type, e.g., dry, normal, oily, combined dry/normal, combined dry/oily, or combined normal/oily skin (the latter two classes hereinafter alternatively referred to as "combination skin").

Persons having an oily skin type or a combination skin type typically manifest an oily and/or shiny skin appearance between cleansings. Following initial cleansing of the skin, this oily or shiny appearance generally increases as the day progresses. In order to avoid such appearance, individuals must throughout the day either cleanse the skin, blot the skin, apply oil absorbing powders to the skin, or take some other measure to minimize the appearance of oil or shine. Therefore, it has been desired in the art to provide topical compositions which reduce sebum synthesis by the sebaceous glands and minimize the appearance of oil and/or shine on the skin, especially oily or combination skin.

Furthermore, in the field of cosmetic or make-up compositions, several topical compositions which are said to be designed for controlling oily and/or shiny skin are known in the art. For example, facial moisturizers and make-up said to have such property are known. However, an oily or a combination skin type presents a particular challenge to the formulation of make-up intended for facial use, including foundations. As oil accumulates on the facial skin of such individuals, oil breakthrough occurs. In other words, the make-up fails to sufficiently mask the oil such that an oily or shiny skin appearance results. As a result, the coverage and wear resistance of the make-up tends to be reduced. It would be desirable to provide a make-up composition that maintains a high degree of coverage and wear resistance after application to all skin types, including oily and combination skin, preferably substantially as originally applied.

While certain formulations have been designed in an attempt to control the oily and/or shiny appearance of skin, there remains a need to provide improved topical compositions for reducing sebum synthesis by the sebaceous glands and minimizing the appearance of skin oil and/or shine. In addition to minimizing oil and/or shine, such compositions should not unacceptably discolor the skin. Therefore, there is a particular need to provide improved skin care compositions and make-up which (i) reduces sebum synthesis by the sebaceous glands, (ii) minimizes the appearance of skin oil and/or shine, (iii) provides and maintains an even (i.e., uniform coverage) complexion and acceptable skin tone for extended periods after application, and/or (iv) which has extended wear resistance after application.

Dehydroacetic acid and its pharmaceutically acceptable salts have heretofore been used as preservatives, antimicrobial agents, and bactericides in cosmetic formulations, food packaging and veterinary drugs. These utilities and many others are further described in the *Final Report on the Safety Assessment of Sodium Dehydroacetate and Dehydroacetic Acid*, Journal of the American College of Toxicology, Vol. 4, No. 3, pp. 123–159 (1985).

It has surprisingly been found that dehydroacetic acid and its pharmaceutically acceptable salts are useful when topically applied for inhibiting sebaceous gland activity. Since the sebaceous gland is a principal source of oil on mammalian skin and scalp, a primary benefit of controlling sebaceous gland activity (e.g., sebum secretion) includes a reduction in the level of oil found in skin and hair. As a result, dehydroacetic acid is useful for regulating the appearance of oily and/or shiny skin, including oily and combination skin. It has also surprisingly been found that topical compositions containing these compounds in the form of a facial make-up composition minimize the appearance of skin oil and/or shine, provide and maintain substantially uniform coverage and an acceptable skin tone for extended periods after application, and/or have extended wear resistance after application.

Because of the ability of dehydroacetic acid to control sebaceous gland activity, it has also been found to be useful in treating acne and related skin disorders in mammalian skin and scalp, such as, eczema, seborrhea, impetigo, psoriasis, rosacea.

It is an object of the present invention to provide topical compositions for inhibiting sebaceous gland activity which results in effectively regulating the oily and/or shiny appearance of mammalian skin, especially facial skin. It is a further object of this invention to provide such topical compositions which regulate the appearance of oily and/or shiny mammalian skin, provide and maintain substantially uniform coverage for extended periods after application to the skin, provide and maintain an acceptable skin tone for extended periods after application to the skin, and/or have extended wear resistance after application to the skin. Another object of the present invention is to provide methods of regulating the appearance of oily and/or shiny mammalian skin and methods of reducing sebum synthesis by the pilosebaceous glands.

It is a further object of the present invention to provide topical compositions for treatment of acne and related skin disorders in mammalian skin and scalp.

Other objects of the subject invention will be apparent from the disclosure which follows.

SUMMARY OF THE INVENTION

The present invention relates to a method of inhibiting sebaceous gland activity in mammalian skin and scalp, such method comprises the step of administering a certain kind of topical composition to the skin or scalp of a mammal susceptible to having excessive sebaceous gland activity. These topical compositions comprise a safe and effective amount of dehydroacetic acid or pharmaceutically-acceptable salts, derivatives, or tautomers thereof, and a dermatologically-acceptable carrier. The present invention also relates to methods of regulating the oily and/or shiny skin appearance using these compositions.

In another embodiment, the present invention also relates to topical compositions for inhibiting sebaceous gland activity. These compositions comprise a safe and effective amount of dehydroacetic acid or pharmaceutically-acceptable salts, derivatives, or tautomers thereof, a sebum absorbing material, and a dermatologically-acceptable carrier. Alternative embodiments relate to topical composition which further comprise sebum spreading reduction materials. Methods of inhibiting excessive sebaceous gland activity using these above compositions are also within the purview of this invention.

In another embodiment, the present invention relates to a topical composition for regulating oily and/or shiny skin appearance. These compositions comprise a safe and effective amount of dehydroacetic acid or pharmaceutically-acceptable salts, derivatives, or tautomers thereof, an oily and/or shiny skin appearance control active, and a dermatologically-acceptable carrier. Methods of regulating oily and/or shiny skin appearance with the above compositions are also within the purview of this invention.

In still another embodiment, the present invention relates to methods and topical compositions for treating acne in mammalian skin or scalp. These compositions comprise a safe and effective amount of dehydroacetic acid or pharmaceutically-acceptable salts, derivatives, or tautomers thereof, an ancillary anti-acne active, and a dermatologically-acceptable carrier. Also included in this embodiment is a method of treating acne with a composition comprising a safe and effective amount of dehydroacetic acid or pharmaceutically-acceptable salts, derivatives, or tautomers thereof, and a dermatologically-acceptable carrier.

All percentages and ratios used herein, unless otherwise indicated, are by weight and all measurements made are at 25° C., unless otherwise designated. The invention hereof can comprise, consist of, or consist essentially of, the essential as well as optional ingredients and components described therein.

DETAILED DESCRIPTION OF THE INVENTION

The compositions of the present invention are useful as topical compositions, i.e., they are suitable for topical administration to mammals. As used herein, "topical" means applied to the surface of the skin or scalp. The compositions of the subject invention are administered topically to a biological subject, i.e., by the direct laying on or spreading of the composition on the skin or scalp of the subject.

The topical compositions comprise a safe and effective amount of dehydroacetic acid (or a pharmaceutically acceptable salt thereof) and a dermatologically-acceptable topical carrier.

As used herein "comprising" means that other steps and ingredients which do not affect the end result can be added. This term encompasses the terms "consisting of" and "consisting essentially of". The phrase "consisting essentially of" means that the composition may include additional ingredients, but only if the additional ingredients do not materially alter the basic and novel characteristics of the claimed compositions or methods.

As used herein, "safe and effective amount" means a sufficient amount of a compound, composition or other material described by this phrase to significantly induce a positive modification in the condition being treated, but low enough to avoid significant side effects (e.g., significant skin irritation or sensitization), within the scope of sound judgment of the skilled artisan. The safe and effective amount of the compound, composition or other material may vary with the particular skin being treated, the age and physical condition of the biological subject being treated, the severity of the condition, the duration of the treatment, the nature of concurrent therapy, the specific compound, composition or other material employed, the particular cosmetically acceptable topical carrier utilized, and like factors within the knowledge and expertise of the skilled artisan.

The term "dermatologically-acceptable," as used herein, means that the compositions or components thereof so described are suitable for use in contact with mammalian skin without undue toxicity, incompatibility, instability, allergic response, and the like.

As used herein, "inhibiting sebaceous gland activity" means preventing, retarding, reducing and/or minimizing the production of sebum.

As used herein, "regulating the oily and/or shiny appearance of skin" means preventing, retarding and/or arresting the appearance of oil and/or shine on the skin. By regulating the oily and/or shiny appearance of the skin, one or more of the following benefits are achieved: there is a noticeable decrease in the visible oil, shine, greasiness, or highlights on the skin; the skin is substantially free from visible oiliness, shine, or highlights; the skin has a substantially matte finish; the user has a more uniform complexion. Regulating the oily and/or shiny appearance of the skin may result in more uniform and lasting coverage of the skin by the composition, increased wear resistance of the composition and/or a decrease in the incidence or severity of skin oil breaking through the composition so as to become visibly apparent. In addition, the resulting reduction of greasiness of the skin (e.g., tactile sensation) also prevents and/or reduces other detrimental effects associated with excessive skin oiliness, such as, itchiness, redness, irritation, and inflammation.

As used herein, "mixtures" is meant to include a simple combination of materials and any compounds that may result from their combination.

I. Dehydroacetic Acid

The compositions of this invention comprise dehydroacetic acid, having the structure:

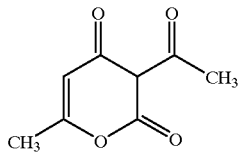

or pharmaceutically acceptable salts, derivatives, or tautomers thereof (hereafter referred to as "dehydroacetic acid or pharmaceutically acceptable salts thereof"), in an amount that is safe and effective for (i) reducing sebum synthesis by the pilosebaceous glands, (ii) regulating the oily and/or shiny appearance of the skin, and (iii) treating acne and other related skin disorders in mammalian skin and scalp. The compositions of the present invention comprise from about 0.1% to about 25% by weight of the composition, preferably from about 0.1% to about 10%, more preferably from about 0.5% to about 5%, and most preferably from about 1% to about 5% of dehydroacetic acid or dermatologically acceptable salts, derivatives, or tautomers thereof.

As used herein, "pharmaceutically acceptable" means that the salts of dehydroacetic are suitable for use in contact with the tissues of mammals to which they will be exposed without undue toxicity, incompatibility, instability, irritation, allergic response, and the like, commensurate with a reasonable benefit/risk ratio. As used herein, "related skin disorders in mammalian skin and scalp" means medical conditions resulting from oiliness of the skin, such as, eczema, seborrhea, impetigo, psoriasis, rosacea. The technical name for dehydroacetic acid is 3-Acetyl-6-methyl-2H-pyran-2,4(3H)-dione and can be commercially purchased under the tradename Unisept DHA ® from Universal Preserv-A-Chem, Inc., located in Brooklyn, N.Y.

Dermatologically acceptable salts include alkali metal salts, such as sodium and potassium; alkaline earth metal salts, such as calcium and magnesium; non-toxic heavy metal salts; ammonium salts; and trialkylammonium salts, such as trimethyammonium and triethylammonium. Sodium, potassium, and ammonium salts of dehydroacetic acid are preferred. Derivatives of dehydroacetic acid include, but are not limited to, any compounds wherein the $CH_3$ groups are individually or in combination replaced by amides, esters, amino groups, alkyls, and alcohol esters. Tautomers of dehydroacetic acid are the isomers of dehydroacetic acid which can change into one another with great ease so that they ordinarily exist in equilibrium. Thus, tautomers of dehydroacetic acid can be described as having the chemical formula $C_8H_8O_4$ and generally having the structure above.

Dehydroacetic acid is water soluble and has no significant formulation issues. Although the activity of dehydroacetic acid in inhibiting sebaceous gland activity is not compromised by pH, risk of eye irritation, however, is expected to increase significantly as formulation pH decreases.

II. Ancillary Actives

The compositions of the present invention can further comprise one or more ancillary actives capable of functioning in different ways to enhance the benefits of dehydroacetic acid and/or to provide other benefits. These ancillary actives (i) enhance the reduction of sebum synthesis, (ii) help regulate the oily and/or shiny appearance of skin, or (iii) provide anti-acne benefits which complement the benefits of dehydroacetic acid.

The ancillary active ingredients useful herein are categorized by their cosmetic and/or therapeutic benefit or their postulated mode of action. However, it is to be understood that the ancillary active ingredients useful herein can in some instances provide more than one cosmetic and/or therapeutic benefit or operate via more than one mode of action. Therefore, classifications herein are made for the sake of convenience and are not intended to limit the active ingredient to that particular application or applications listed.

A. Oil Control Agents

Sebum absorbing materials: The compositions of the present invention can also contain oil/sebum absorbing materials also known as sequestering agents. Nonlimiting examples are clays (e.g., bentonite), talcs, silicas, starches, polymeric absorbents (e.g., MICROSPONGES 5647 and POLYTRAP, both commercially available from Advanced Polymer Systems, Inc. of Redwood City, Calif., USA), and other such materials. MICROSPONGES 5647 is a polymer mixture derived from styrene, methyl methacrylate, and hydrogel acrylate/methacrylate. Other useful sebum absorbing materials are disclosed in U.S. Pat. No. 4,940,578, to Yoshihara, T. et al., issued Jul. 10, 1990; U.S. Pat. No. 4,885,109 to Umemoto, I. et al., issued Dec. 5, 1989; U.S. Pat. No. 4,536,399, to Flynn, R. G. et al., issued Aug. 20, 1985; U.S. Pat. No. 4,489,058, to Lay, G. E. et al., issued Dec. 18, 1984; U.S. Pat. No. 4,619,826, to Lay, G. E. et al., issued Oct. 28, 1986; U.S. Pat. No. 4,388,301, to Klein, R. W., issued Jun. 14, 1983; and U.S. Pat. No. 4,000,317, to Menda, W. C. et al., issued Dec. 28, 1976; U.S. Pat. No. 4,294,823, to Elliott, T. J. et al., issued Oct. 13, 1981; U.S. Pat. No. 5,145,685, to Carmody, W. J., issued Sep. 8, 1992; U.S. Pat. No. 5,386,003, to Greene, C. J. et al., issued Jan. 31, 1995; PCT Application WO 92/00724, published Jan. 23, 1992; all incorporated herein by reference.

Sebum migration reduction material: The compositions of the present invention can also contain materials which reduce sebum spreadability. By reduction of sebum spreading/migration is meant that these materials retard or arrest the migration or movement of sebum from the areas immediately near the sebaceous gland to the rest of the skin or hair. Nonlimiting examples are cocamidopropyl hydroxysultaine in combination with a quaternary halide of N,N,N-trialkylaminoalkylene gluconamide, as described in U.S. Pat. No. 4,534,964, to Herstein, M. S. et al., issued Aug. 13, 1985; and further in combination with ammonium lauryl sulfate and triethanolamine lauryl sulfate, as described in U.S. Pat. No. 4,529,588, to Smith, W. P. et al., issued Jul. 16, 1985; and straight chain dimethyl silicone polymer having the formula:

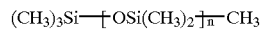

wherein n is a positive integer sufficient to provide a silicone polymer having a molecular weight of about 50,000 or more and a viscosity of about 10,000 centistokes or more, as described in U.S. Pat. No. 4,515,784, to Bogardus, R. E. et al., issued May 7, 1985; all of which are incorporated herein by reference in their entirety.

B. Ancillary Sebosupressive Actives

The compositions of the present invention can comprise one or more suitable ancillary sebosupressive actives (e.g., in addition to dehydroacetic acid) in an amount that is safe and effective for regulating the oily and/or shiny appearance (hereinafter referred to as "OSA") of the skin. Without being limited by theory, it is believed that ancillary sebosuppressive actives decrease the sebum output of the pilosebaceous ducts of the skin, thereby reducing surface oiliness. Suitable OSA actives are those which effectively regulate the oily and/or shiny appearance of skin without unacceptably discoloring the skin, e.g., unacceptably causing reddening or flushing of the skin. Suitable ancillary sebosuppressive actives are described in Karg, G. et al., "Sebosupression," *Cosmetics and Toiletries*, vol. 102, pp. 140–146 (April 1987); U.S. Pat. No. 4,593,021, to Hsia, S. L. et al., issued Jun. 3, 1986; U.S. Pat. No. 4,587,235, to Bittler, D. et al., issued May 6, 1986; U.S. Pat. No. 4,529,587, to Green, M. R., issued Jul. 16, 1985; U.S. Pat. No. 4,210,654 to Bauer et al., issued Jul. 1, 1980; U.S. Pat. No. 4,016,287, to Eberhardt et al., issued Apr. 5, 1977; and U.S. Pat. No. 5,587,176, to Warren, R. et al., issued Dec. 24, 1996; all of which are incorporated herein by reference in their entirety.

Compounds that possess significant vasodilatory properties are typically unsuitable for use as ancillary actives. Such vasodilatory compounds tend to cause unacceptable flushing or reddening of the skin such that their use, especially in facial applications, is not desirable. For example, known vasodilators such as nicotinic acid are not suitable for use herein. Although not preferred, such vasodilatory compounds may be added in amounts which would not trigger their vasodilatory properties. Vasodilatory compounds may be added to the compositions of the present invention preferably from about 0.0001% to about 1%, more preferably from about 0.001% to about 0.1%. The exact amount will depend on the particular vasodilatory compound utilized since such agents very widely in potency.

Preferred compositions of this invention comprise as ancillary sebosuppressive actives one or more compounds selected from the group consisting of vitamin B3 compound, tocopherol nicotinate, pyridoxine, panthenol, pantothenic acid, tioxolone (6-Hydro-2-oxo-1,3-benzoxathiole), hesperetin, and mixtures thereof. As used herein, "vitamin B3 compound" means a compound having the formula:

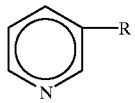

wherein R is —CONH2 (e.g., niacinamide), —COOH (e.g., nicotinic acid) or —CH20H (e.g., notinyl alcohol); and derivatives hereof; and salts of any of the foregoing. Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

In a preferred embodiment, the ancillary sebosuppressive actives are substantially pure. By substantially pure it is meant that the compound described by that phase is at least 90% pure, at least more preferably 95% pure, most preferably 99% pure.

In a preferred embodiment, the ancillary sebosuppressive active comprises niacinamide, which is more preferably substantially pure niacinamide. Thus, the ancillary active may consist essentially of:

(a) niacinamide; or (b) a mixture of (i) niacinanide and (ii) a compound selected from the group consisting of panthenol, pantothenic acid, pyridoxine, tioxolone, and hesperetin.

Preferably, the composition comprises from about 0.01% to about 25%, by weight, of sebosuppressive active, more preferably from about 0.1% to about 10%, even more preferably from about 1% to about 5%, most preferably from about 2% to about 5%.

In an especially preferred embodiment, the topical composition comprises from about 2% to about 5%, by weight, of niacinamide, which is preferably substantially pure niacinamide.

When niacinamide (a vitamin $B_3$ compound) is being used in the present invention the following cautionary notes must be observed. It has been found that certain compounds may negatively impact the skin benefits otherwise provided by the vitamin $B_3$ compound. Such compounds include ascorbic acid and N-acetyl cysteine. Without intending to be bound or limited by theory, it is believed that these compounds may form large or poorly soluble complexes, e.g., salts, with the vitamin $B_3$ compound which reduce the availability of the vitamin $B_3$ compound to the skin. Such complexes are believed to have a relatively high molecular weight or are poorly soluble which decreases their availability to the skin. Therefore, in one embodiment of the invention, the compositions do not contain these compounds or compounds which are capable of forming similar complexes with the vitamin $B_3$ compound. In another embodiment, where the composition contains these compounds or compounds which are capable of forming complexes with the vitamin $B_3$ compound, one or more of the approaches described herein for minimizing or preventing the formation of undesirable complexes are preferred.

For example, the impact of such compounds on the efficacy of the vitamin $B_3$ compound decreases with a decrease in pH such that pH adjustments can be employed to minimize or obviate such effects. For example, when the composition contains N-acetyl-L-cysteine, the pH of the composition is preferably adjusted to from about 2 to about 5, more preferably from about 3 to about 4. The adjustment of pH to obviate substantial impacts on efficacy is well within the level of ordinary skill in the art.

C. Ancillary Anti-Acne Actives

Sebum also plays an important role in the pathogenesis of acne. The ductal increase in sebum production results in an increase in certain bacteria, notably Propionibacterium acnes, which can initiate a primary follicular inflammation (e.g., acne). Because of the role that sebum plays in the etiology of acne, preventive measures are primarily concerned with reduction in the quantity of sebum present on the skin and underlying tissue. Since dehydroacetic acid has been surprisingly found to reduce sebum synthesis, the compositions of the present invention can suitably be used to treat acne and can contain an ancillary anti-acne active selected from the group consisting of antimicrobial agents, antiandrogens, comedolytic/keratolytic agents, and anti-inflammatory agents.

As used herein "treating acne" means preventing, retarding and/or arresting the process of acne formation, and/or clearing or healing existing lesions.

As used herein, "anti-acne active" means an active capable of preventing, retarding and/or arresting the process of acne formation, and/or clearing or healing existing lesions.

Comedolytic/keratolytic agents: In a preferred composition useful in the subject invention, a comedolytic agent and/or a keratolytic agents are included as an active along with the dehydroacetic acid. As used herein, the term "comedolytic agent" refers to any compound capable of rupturing a comedo. As used herein, the term "keratolytic agent" refers to any compound capable of breaking apart keratinocytes resulting in exfoliation of the epidermis.

A safe and effective amount of a comedolytic agent and/or a keratolytic agent may be added to the composition useful in the subject invention, preferably from about 0.05% to about 10% , more preferably from about 0.1% to about 5%.

Preferred comedolytic and keratolytic agents useful in the subject invention are selected from the group consisting of retinoids, salicylic acid, lactic acid, glycolic acid, cetyl betaine, sulfur, and resorcinol. Especially preferred is a combination cetyl betaine and salicylic acid.

In a preferred acne-treating composition useful in the subject invention, a retinoid, preferably retinoic acid, is included as an active along with the dehydroacetic acid. The inclusion of a retinoid increases the acne-treating benefits of the composition. A safe and effective amount of a retinoid may be added to the compositions useful in the subject invention, preferably from about 0.001% to about 5% by weight of the composition, more preferably from about 0.01% to about 5%, most preferably from about 0.01% to about 3%. As used herein, "retinoid" includes all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid.

Retinoids are also useful in providing unexpected benefits in regulating skin condition, especially in therapeutically regulating signs of skin aging, more especially wrinkles, lines, and pores. The retinoid for this particular benefit is preferably retinol, retinol esters (e.g., $C_2$–$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. Nos. 4,677,120, issued Jun. 30, 1987 to Parish et al.; 4,885,311, issued Dec. 5, 1989 to Parish et al.; 5,049,584, issued Sep. 17, 1991 to Purcell et al.; 5,124,356, issued Jun. 23, 1992 to Purcell et al.; and Reissue 34,075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). One or more retinoids may be used herein. Preferred retinoids are retinol, retinyl palmitate, retinyl acetate, retinyl propionate, retinal and combinations thereof. More preferred are retinol and retinyl propionate.

The retinoid may be included as the substantially pure material, or as an extract obtained by suitable physical and/or chemical isolation from natural (e.g., plant) sources. The retinoid is preferably substantially pure, more preferably essentially pure.

In a preferred embodiment, the compositions of the present invention contain a retinoid in combination with a vitamin $B_3$ compound and dehydroacetic acid. The vitamin $B_3$ compound and retinoid provide unexpected benefits in reducing sebum synthesis and regulating skin condition, especially in therapeutically regulating signs of skin aging, more especially wrinkles, lines, and pores (hereinafter referred to as "regulating skin condition"). Without intending to be bound or otherwise limited by theory, it is believed that the vitamin $B_3$ compound increases the conversion of certain retinoids to trans-retinoic acid, which is believed to be the biologically active form of the retinoid, to provide synergistic regulation of skin condition (namely, increased conversion for retinol, retinol esters, and retinal). In addition, the vitamin $B_3$ compound unexpectedly mitigates redness, inflammation, dermatitis and the like which may otherwise be associated with topical application of retinoid (often referred to, and hereinafter alternatively referred to as "retinoid dermatitis"). Furthermore, the combined vitamin $B_3$ compound and retinoid tend to increase the amount and activity of thioredoxin, which tends to increase collagen expression levels via the protein AP-1. Therefore, the present invention enables reduced active levels, and therefore reduced potential for retinoid dermatitis, while retaining significant positive skin conditioning benefits. In addition, higher levels of retinoid may still be used to obtain greater skin conditioning efficacy, without undesirable retinoid dermatitis occurring.

The compositions of this invention may contain a safe and effective amount of the retinoid, such that the resultant composition is safe and effective for reducing sebum synthesis, preventing acne, and regulating skin condition. The compositions preferably contain from about 0.001% to about 5% by weight of the composition, more preferably from about 0.01% to about 5%, most preferably from about 0.01% to about 3%, retinoid. Retinol is most preferably used in an amount from about 0.01% to about 0.15%; retinol esters are most preferably used in an amount from about 0.01% to about 2% (e.g., about 1%); retinoic acids are most preferably used in an amount from about 0.01% to about 0.25%; tocopheryl-retinoate [tocopherol ester of retinoic acid (trans- or cis), adapalene {6-[3-(1-adamantyl)-4-methoxyphenyl]-2-naphthoic acid}, and tazarotene are most preferably used in an amount from about 0.01% to about 2%. When the composition contains a retinoid, the vitamin $B_3$ compound is preferably used in an amount of from about 0.1% to about 10%, more preferably from about 2% to about 5%.

Antimicrobial agents: In a preferred acne-treating composition useful in the subject invention, an antimicrobial agent is included as an active along with the dehydroacetic acid. The inclusion of an antimicrobial agent increases the acne-treating benefits of the composition. As used herein, "antimicrobial agent" means a compound capable of destroying microbes, preventing the development of microbes or preventing the pathogenic action of microbes.

A safe and effective amount of an antimicrobial agent may be added to compositions of the subject invention, preferably from about 0.001% to about 10%, more preferably from about 0.01% to about 5%, also from about 0.05% to about 2% or from about 0.05% to about 1% of the compositions. Preferred antimicrobial agents useful in the subject invention are benzoyl peroxide, erythromycin, tetracycline, clindamycin, and azelaic acid.

Anti-inflammatory agents: An anti-inflammatory agent can be included as an active along with dehydroacetic acid, for treatment of acne. A safe and effective amount of an anti-inflammatory agent may be added to the compositions of the subject invention, preferably from about 0.1% to about 10%, more preferably from about 0.5% to about 5%, by weight of the composition. The anti-inflammatory agent enhances the skin appearance benefits of the present invention, e.g., such agents contribute to a more uniform and acceptable skin tone. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triarncinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, reference may be had to standard texts, including *Anti-inflammatory and Anti-Rheumatic Drug*, K. D. Rainsford, Vol. I–III, CRC Press, Boca Raton, (1985), and *Anti-inflammatory Agents, Chemistry and Pharmacology*, 1, R. A. Scherrer, et al., Academic Press, New York (1974), each incorporated herein by reference.

Specific non-steroidal anti-inflammatory agents useful in the composition invention include, but are not limited to:

1) the oxicams, such as piroxicam, isoxicam, tenoxicam, sudoxicam, and CP-14,304;

2) the salicylates, such as aspirin, disalcid, benorylate, trilisate, safapryn, solprin, diflunisal, and fendosal;

3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;

4) the fenamates, such as mefenamic, meclofenamic, flufenamic, niflumic, and tolfenamic acids;

5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and 6) the pyrazoles, such as phenylbutazone, oxyphenbutazone, feprazone, azapropazone, and trimethazone, 7) anti-oxidants, such as ascorbic acid (vitamin C) and its salts, ascorbyl esters of fatty acids, ascorbic acid derivatives (e.g., magnesium ascorbyl phosphate), tocopherol (vitamin E), tocopherol sorbate, other esters of tocopherol (e.g., acetate, succinate, linoleate).

Mixtures of these non-steroidal anti-inflammatory agents may also be employed, as well as the dermatologically acceptable salts and esters of these agents. For example, etofenamate, a flufenamic acid derivative, is particularly useful for topical application. Of the nonsteroidal anti-inflammatory agents, ibuprofen, aspirin, naproxen, flufenamic acid, mefenamic acid, meclofenamic acid, piroxicam and felbinac are preferred; ibuprofen, naproxen, flufenamic acid, ascorbic acid, and tocopherol sorbate are most preferred.

Finally, so-called "natural" anti-inflammatory agents are useful in methods of the subject invention. For example, candelilla wax, alpha bisabolol, aloe vera, Manjistha (extracted from plants in the genus Rubia, particularly *Rubia Cordifolia*), Guggal (extracted from plants in the genus Comminhora, particularly *Commiphora Mukul*), and green tea extract, may be used.

Antiandrogens: In a preferred acne-treating composition useful in the subject invention, an antiandrogen is included as an active along with dehydroacetic acid. As used herein, "anti-androgen" means a compound capable of correcting androgen-related disorders by interfering with the action of androgens at their target organs. The target organ for the subject invention is mammalian skin.

A safe and effective amount of an antiandrogen may be added to the compositions useful in the subject invention, preferably from about 0.001% to about 5%, more preferably from about 0.001% to about 1%.

Antiandrogens which are androgen receptor antagonists, as well as, antiandrogens which are 5-α reductase inhibitors are useful in the compositions of the subject invention. Examples of such antiandrogens are more fully disclosed in U.S. Pat. No. 4,888,336, Holt, Metcalf and Levy, issued Dec. 19, 1989; U.S. Pat. No. 5,110,939, Holt Metcalf and Levy; issued May 5, 1992; U.S. Pat. No. 5,120,742, Rasmusson and Reynolds, issued Jun. 9, 1992; and U.S. Pat. No. 4,859,681, Rasmusson and Reynolds, issued Aug. 22, 1989; all incorporated herein by reference. See also Stewart, M. and P. Pochi, *Antiandrogens and the Skin*, International Society of Tropical Dermatology, Vol. 17, No. 3, pp. 167–179 (1978); incorporated herein by reference in its entirety.

Preferred antiandrogens useful for compositions of the subject invention are cyproterone acetate, fmasteride, chlormadinon acetate, 17α propylmesterolone, 17-α estradiol acetate, dienoestrol diacetate, estradiol benzoate, inocoterone acetate, spirono-lactone, 11-α hydroxyprogestrone, and mixtures thereof.

III. Dermatologically Acceptable Carrier

The compositions of the present invention comprise a dermatologically acceptable carrier within which dehydroacetic acid is incorporated to enable dehydroacetic acid, ancillary actives, and optional other actives to be delivered to the skin at an appropriate concentration. The carrier can thus act as a diluent, dispersant, solvent, or the like for the active(s) which ensures that it can be applied to and distributed evenly over the selected target at an appropriate concentration.

The carrier may contain one or more dermatologically acceptable solid, semi-solid or liquid fillers, diluents, solvents, extenders and the like. The carrier may be solid, semi-solid or liquid. The carrier can itself be inert or it can possess dermatological benefits of its own. Concentrations of the carrier can vary with the carrier selected and the intended concentrations of the essential and optional components.

Suitable carriers include conventional or otherwise known carriers that are dermatologically acceptable. The carrier should also be physically and chemically compatible with the essential components described herein, and should not unduly impair stability, efficacy or other use benefits associated with the compositions of the present invention. Preferred components of the compositions of this invention should be capable of being commingled in a manner such that there is no interaction which would substantially reduce the efficacy of the composition under ordinary use situations.

The type of carrier utilized in the present invention depends on the type of product form desired for the composition. The topical compositions useful in the subject invention may be made into a wide variety of product forms such as are known in the art. These include, but are not limited to, lotions, creams, gels, sticks, sprays, ointments, pastes, mousses and cosmetics (e.g., solid, semi-solid, or liquid make-up, including foundations, eye-makeup, pigmented or non-pigmented lip treatments, e.g., lipsticks, and the like). These product forms may comprise several types of carriers including, but not limited to, solutions, aerosols, emulsions, gels, solids, and liposomes.

Preferred carriers contain a dermatologically acceptable, hydrophilic diluent. As used herein, "diluent" includes materials in which dehydroacetic acid can be dispersed, dissolved, or otherwise incorporated. Hydrophilic diluents include water, organic hydrophilic diluents such as lower monovalent alcohols (e.g., $C_1$–$C_4$) and low molecular weight glycols and polyols, including propylene glycol, polyethylene glycol (e.g., Molecular Weight 200–600 g/mole), polypropylene glycol (e.g., Molecular Weight 425–2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof. Water is a preferred diluent. The composition preferably comprises from about 75% to about 99.99% of the hydrophilic diluent and dehydroacetic acid in the above described amounts. Examples of suitable carriers which high hydrophobic diluents are described in U.S. Pat. No. 5,380,528, to Alban, N. C. et al., issued Jan. 10, 1995, U.S. Pat. No. 5,420,118, to Alban, N. C. et al., issued May 30, 1995, both incorporated by reference herein in their entirety.

Aerosols according to the subject invention can be formed by adding a propellant to a solution such as described above. Exemplary propellants include chloro-fluorinated lower molecular weight hydrocarbons. Additional propellants that are useful herein are described in Sagarin, *Cosmetics Science and Technology*, 2nd Edition, Vol. 2, pp. 443–465 (1972), incorporated herein by reference. Aerosols are typically applied to the skin as a spray-on product.

Preferred carriers comprise an emulsion such as oil-in-water emulsions, water-in-oil emulsions, and water-in-silicone emulsions. As will be understood by the skilled artisan, a given component will distribute primarily into either the water or oil/silicone phase, depending on the water solubility/dispersibility of the component in the composition. Dehydroacetic acid distributes primarily into the aqueous phase. Oil-in-water emulsions are especially preferred.

Emulsions according to the present invention generally contain a solution as described above and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and *McCutcheon's Detergents and Emulsifiers*, North American Edition, pages 317–324 (1986), each incorporated herein by reference.

The emulsion may also contain an anti-foaming agent to minimize foaming upon application to the skin. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less.

Preferred water-in-silicone and oil-in-water emulsions are described in greater detail below.

a) Water-in-silicone Emulsion

Water-in-silicone emulsions contain a continuous silicone phase and a dispersed aqueous aphase.

(i) Continuous Silicone Phase

Preferred water-in-silicone emulsions of the present invention comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase contains a polyorganosiloxane oil. A preferred water-in-silicone emulsion system is formulated to provide an oxidatively stable vehicle for the optional retinoid. The continuous silicone phase of these preferred emulsions comprises between about 50% and about 99.9% by weight of organopolysiloxane oil and less than about 50% by weight of a non-silicone oil. In an especially preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and most preferably less than about 2%, by weight of the continuous silicone phase. These preferred emulsion systems provide more oxidative stability to the retinoid over extended periods of time than comparable water-in-oil emulsions containing lower concentrations of the polyorganosiloxane oil. Concentrations of non-silicone oils in the continuous silicone phase are minimized or avoided altogether so as to further enhance oxidative stability of the selected retinoid in the compositions. Water-in-silicone emulsions of this type are described in copending U.S. patent application Ser. No. 08/570,275, filed Dec. 11, 1995, in the names of Joseph Michael Zukowski, Brent William Mason, Larry Richard Robinson and Greg George Hillebrand, incorporated herein by reference.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Such polyalkylsiloxanes can be represented by the general chemical formula $R_3SiO[R_2SiO]_xSiR_3$ wherein R is an alkyl group having from one to about 30 carbon atoms (preferably R is methyl or ethyl, more preferably methyl; also mixed alkyl groups can be used in the same molecule), and x is an integer from 0 to about 10,000, chosen to achieve the desired molecular weight which can range to over about 10,000,000. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Suitable dimethicones include those represented by the chemical formula $(CH_3)_3SiO[(CH_3)_2SiO]_x[CH_3RSiO]_ySi(CH_3)_3$ wherein R is straight or branched chain alkyl having from two to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes suitable for use in the composition include those represented by the chemical formula $[SiR_2—O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6).

Also useful are materials such as trimethylsiloxysilicate, which is a polymeric material corresponding to the general chemical formula $[(CH_2)_3SiO_{1/2}]_x[SiO_2]y$, wherein x is an integer from about 1 to about 500 and y is an integer from about 1 to about 500. A commercially available trimethylsiloxysilicate is sold as a mixture with dimethicone as Dow Corning® 593 fluid.

Dimethiconols are also suitable for use in the composition. These compounds can be represented by the chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from the group consisting of polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

As stated above, the continuous silicone phase may contain one or more non-silicone oils. Concentrations of non-silicone oils in the continuous silicone phase are preferably minimized or avoided altogether so as to further enhance oxidative stability of the selected retinoid in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

(ii) Dispersed Aqueous Phase

The topical compositions of the present invention comprise from about 30% to about 90%, more preferably from about 50% to about 85%, and most preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention will typically comprise from about 25% to about 90%, preferably from about 40% to about 80%, more preferably from about 60% to about 80%, water in the dispersed aqueous phase by weight of the composition.

(iii) Emulsifier for Dispersing the Aqueous Phase

The water-in-silicone emulsions of the present invention preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, non-silicon-containing emulsifiers, and mixtures thereof, known by those skilled in the art for use in topical personal care products. Preferably these emulsifiers have an HLB value of or less than about 14, more preferably from about 2 to about 14, and most preferably from about 4 to about 14. Emulsifiers having an HLB value outside of these ranges can be used in combination with other emulsifiers to achieve an effective weighted average HLB for the combination that falls within these ranges.

Silicone emulsifiers are preferred. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2–C30 pendant side chains. Still other useful dimethicone copolyols include materials having various cationic, anionic, amphoteric, and zwitterionic pendant moieties.

The dimethicone copolyol emulsifiers useful herein can be described by the following general structure:

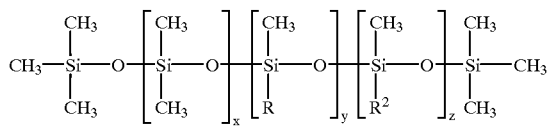

wherein R is C1–C30 straight, branched, or cyclic alkyl and $R^2$ is selected from the group consisting of

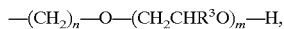

and

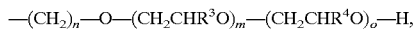

wherein n is an integer from 3 to about 10; $R^3$ and $R^4$ are selected from the group consisting of H and C1–C6 straight or branched chain alkyl such that $R^3$ and $R^4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone surfactants as depicted in the structures in the previous paragraph wherein $R^2$ is:

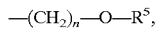

wherein $R^5$ is a cationic, anionic, amphoteric, or zwitterionic moiety.

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant C2–C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, diemethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See *International Cosmetic Ingredient Dictionary*, Fifth Edition, 1993, which is incorporated by reference herein in its entirety.

Dimethicone copolyol emulsifiers useful herein are described, for example, in U.S. Pat. No. 4,960,764, to Figueroa, Jr. et al., issued Oct. 2, 1990; European Patent No. EP 330,369, to SanoGueira, published Aug. 30, 1989; G. H. Dahms, et al., "New Formulation Possibilities Offered by Silicone Copolyols," *Cosmetics & Toiletries*, vol. 110, pp. 91–100, March 1995; M. E. Carlotti et al., "Optimization of W/O—S Emulsions And Study Of The Quantitative Relationships Between Ester Structure And Emulsion Properties," *J. Dispersion Science And Technology*, 13(3), 315–336 (1992); P. Hameyer, "Comparative Technological Investigations of Organic and Organosilicone Emulsifiers in Cosmetic Water-in-Oil Emulsion Preparations," HAPPI 28(4), pp. 88–128 (1991); J. Smid-Korbar et al., "Efficiency and usability of silicone surfactants in emulsions," *Provisional Communication, International Journal of Cosmetic Science*, 12, 135–139 (1990); and D. G. Krzysik et al., "A New Silicone Emulsifier For Water-in-Oil Systems," *Drug and Cosmetic Industry*, vol. 146(4) pp. 28–81 (April 1990); incorporated by reference herein in their entirety.

Among the non-silicone-containing emulsifiers useful herein are various non-ionic and anionic emulsifying agents such as sugar esters and polyesters, alkoxylated sugar esters and polyesters, C1–C30 fatty acid esters of C1–C30 fatty alcohols, alkoxylated derivatives of C1–C30 fatty acid esters of C1–C30 fatty alcohols, alkoxylated ethers of C1–C30 fatty alcohols, polyglyceryl esters of C1–C30 fatty acids, C1–C30 esters of polyols, C1–C30 ethers of polyols, alkyl phosphates, polyoxyalkylene fatty ether phosphates, fatty acid amides, acyl lactylates, soaps, and mixtures thereof. Other suitable emulsifiers are described, for example, in McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these references are incorporated herein by reference in their entirety.

Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG- 100 stearate, and mixtures thereof.

b) Oil-in-Water Emulsions

Other preferred topical carriers include oil-in-water emulsions, having a continuous aqueous phase and a hydrophobic, water-insoluble phase ("oil phase") dispersed therein. Examples of suitable carriers comprising oil-in-water emulsions are described in U.S. Pat. No. 5,073,371, to Turner, D. J. et al., issued Dec. 17, 1991, and U.S. Pat. No. 5,073,372, to Turner, D. J. et al., issued Dec. 17, 1991, both incorporated herein by reference in their entirety. An especially preferred oil-in-water emulsion, containing a structuring agent, hydrophilic surfactant and water, is described in detail hereinafter.

(i) Structuring Agent

A preferred oil-in-water emulsion comprises a structuring agent to assist in the formation of a liquid crystalline gel network structure. Concentrations of such structuring agents are from about 1% to about 20%, preferably from about 1% to about 10%, more preferably from about 3% to about 9% by weight of the topical carrier.

Suitable structuring agents are those selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 45° C.

Preferred structuring agents include stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from the group consisting of stearyl alcohol, cetyl alcohol, behenyl alcohol, steareth-2, and mixtures thereof. Most preferred is steareth-2, available under the tradename of Brij® 72 from ICI Americas.

(ii) Hydrophilic Surfactant

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water.

Suitable surfactants include any of a wide variety of known cationic, anionic, zwitterionic, and amphoteric surfactants. See, *McCutcheon's, Deterents and Emulsifiers*, North American Edition (1986), published by Allured Publishing Corporation; U.S. Pat. No. 5,011,681; U.S. Pat. No. 4,421,769; and U.S. Pat. No. 3,755,560; these references are incorporated herein by reference in their entirety.

The exact surfactant chosen will depend upon the pH of the composition and the other components present.

Preferred are cationic surfactants, especially dialkyl quaternary ammonium compounds, examples of which are described in U.S. Pat. No. 5,151,209; U.S. Pat. No. 5,151,210; U.S. Pat. No. 5,120,532; U.S. Pat. No. 4,387,090; U.S. Pat. No. 3,155,591; U.S. Pat. No. 3,929,678; U.S. Pat. No. 3,959,461; *McCutcheon's, Detergents& Emulsifiers*, (North American edition 1979) M.C. Publishing Co.; and Schwartz, et al., *Surface Active Agents, Their Chemistry and Technology*, New York: Interscience Publishers, 1949; which descriptions are incorporated herein by reference. The cationic surfactants useful herein include cationic ammonium salts such as those having the formula:

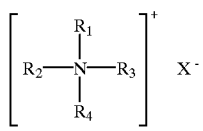

wherein $R_1$, is an alkyl group having from about 12 to about 30 carbon atoms, or an aromatic, aryl or alkaryl group having from about 12 to about 30 carbon atoms; $R_2$, $R_3$, and $R_4$ are independently selected from hydrogen, an alkyl group having from about 1 to about 22 carbon atoms, or aromatic, aryl or alkaryl groups having from about 12 to about 22 carbon atoms; and X is any compatible anion, preferably selected from the group consisting of chloride, bromide, iodide, acetate, phosphate, nitrate, sulfate, methyl sulfate, ethyl sulfate, tosylate, lactate, citrate, glycolate, and mixtures thereof. Additionally, the alkyl groups of $R_1$, $R_2$, $R_3$, and $R_4$ can also contain ester and/or ether linkages, or hydroxy or amino group substituents (e.g., the alkyl groups can contain polyethylene glycol and polypropylene glycol moieties).

More preferably, $R_1$ is an alkyl group having from about 12 to about 22 carbon atoms; $R_2$ is selected from H or an alkyl group having from about 1 to about 22 carbon atoms; $R_3$ and $R_4$ are independently selected from H or an alkyl group having from about 1 to about 3 carbon atoms; and X is as described previously.

Most preferably, $R_1$ is an alkyl group having from about 12 to about 22 carbon atoms; $R_2$, $R_3$, and $R_4$ are selected from H or an alkyl group having from about 1 to about 3 carbon atoms; and X is as described previously.

Alternatively, other useful cationic emulsifiers include amino-amides, wherein in the above structure $R_1$ is alternatively $R_5CONH-(CH_2)_n$, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the $C_{12}$ to $C_{30}$ alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the $C_{16}$ to $C_{18}$ range. The term "coconut" refers to an alkyl group derived from a coconut fatty acid, which generally have mixtures of alkyl chains in the $C_{12}$ to $C_{14}$ range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. An example of a quaternary ammonium compound having an alkyl group with an ester linkage is ditallowyl oxyethyl dimethyl ammonium chloride.

More preferred cationic surfactants are those selected from the group consisting of behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldiammonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Most preferred cationic surfactants are those selected from the group consisting of behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, and mixtures thereof.

A preferred combination of cationic surfactant and structuring agent is behenamidopropyl PG dimonium chloride and/or behenyl alcohol, wherein the ratio is preferably optimized to maintained to enhance physical and chemical stability, especially when such a combination contains ionic and/or highly polar solvents. This combination is especially useful for delivery of sunscreening agents such as zinc oxide and octyl methoxycinnamate.

A wide variety of anionic surfactants are also useful herein. See, e.g., U.S. Pat. No. 3,929,678, to Laughlin et al., issued Dec. 30, 1975, which is incorporated herein by reference in its entirety. Nonlimiting examples of anionic surfactants include the alkoyl isethionates, and the alkyl and alkyl ether sulfates. The alkoyl isethionates typically have the formula $RCO-OCH_2CH_2SO_3M$ wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, sodium stearoyl isethionate, and mixtures thereof.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

$$R_1-SO_3-M$$

wherein $R_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and β-alkyloxy alkane sulfonates. Examples of these materials are sodium lauryl sulfate and ammonium lauryl sulfate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8-C_{18}$) and one contains an anionic water solubilizing group, e.g., carboxy, sulfonate, sulfate, phosphate, or phosphonate. Examples are alkyl imino acetates, and iminodialkanoates and aminoalkanoates of the formulas $RN[CH_2)_mCO_2M]_2$ and $RNH(CH_2)_mCO_2M$ wherein m is from 1 to 4, R is a $C_8-C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as coamidopropyl PG-dimonium chloride phosphate (commercially available as Monaquat PTC, from Mona Corp.).

Also useful herein as amphoteric or zwitterionic surfactants are the betaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

(iii) Water

The preferred oil-in-water emulsion comprises from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The topical compositions of the subject invention, including but not limited to lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. Sagarin, *Cosmetics, Science and Technology*, 2nd Edition, Vol. 1, pp. 32–43 (1972), incorporated herein by reference, contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the present invention generally comprise a solution carrier system and one or more emollients. Lotions typically comprise from about 1% to about 20%, preferably from about 5% to about 10%, of emollient; from about 50% to about 90%, preferably from about 60% to about 80%, water; and dehydroacetic acid in the above described amounts. A cream typically comprises from about 5% to about 50%, preferably from about 10% to about 20%, of emollient; from about 45% to about 85%, preferably from about 50% to about 75%, water; and dehydroacetic acid in the above described amounts.

Ointments of the present invention may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent, such as described in Sagarin, *Cosmetics, Science and Technoloy*, 2nd Edition, Vol. 1, pp. 72–73 (1972), incorporated herein by reference, and/or an emollient. For example, an ointment may comprise from about 2% to about 10% of an emollient; from about 0.1% to about 2% of a thickening agent; and dehydroacetic acid in the above described amount.

Compositions of this invention useful for cleansing ("cleansers") are formulated with a suitable carrier, e.g., as described above, and preferably contain, in addition to dehydroacetic acid in the above described amounts, from about I% to about 90%, more preferably from about 5% to about 10%, of a dermatologically acceptable surfactant. The surfactant is suitably selected from anionic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety, for exemplary surfactants useful herein. Examples of a broad variety of additional surfactants useful herein are described in *McCutcheon's Detergents and Emulsifiers*, North American Edition (1986), published by Allured Publishing Corporation, which is incorporated herein by reference in its entirety. The cleansing compositions can optionally contain, at their art-established levels, other materials which are conventionally used in cleansing compositions.

The physical form of the cleansing compositions is not critical. The compositions can be, for example, formulated as toilet bars, liquids, shampoos, bath gels, hair conditioners, hair tonics, pastes, or mousses. Toilet bars are most preferred since this is the form of cleansing agent most commonly used to wash the skin. Rinse-off cleansing compositions, such as shampoos, require a delivery system adequate to deposit sufficient levels of actives on the skin and scalp. A preferred delivery system involves the use of insoluble complexes. For a more complete disclosure of such delivery systems, see U.S. Pat. No. 4,835,148, Barford et al., issued May 30, 1989, incorporated herein by reference in its entirety.

As used herein, the term "foundation" refers to a liquid, semi-liquid, semi-solid, or solid skin cosmetic which includes, but is not limited to lotions, creams, gels, pastes, cakes, and the like. Typically the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present invention include a dermatologically acceptable carrier for dehydroacetic acid and may include conventional ingredients such as oils, colorants, pigments, emollients, fragrances, waxes, stabilizers, and the like. Exemplary carriers and such other ingredients which are suitable for use herein are described, for example, in copending patent application Ser. No. 08/430,961, filed on Apr. 28, 1995 in the names of Marcia L. Canter, Brain D. Barford, and Brian D. Hofrichter, and U.K. Patent Application GB 2274585-A, published on Jan. 23, 1993, both incorporated herein by reference.

The compositions of the present invention are preferably formulated to have a pH of 10.5 or below. The pH values of these compositions preferably range from about 2 to about 10.5, more preferably from about 3 to about 8, even more preferably from about 4 to about 7, and also from about 4.5 to about 5.5.

IV. Optional Ingredients

The topical compositions of the present invention may comprise a wide variety of optional components (e.g., ingredients conventionally used in the art of skin care compositions, including but not limited to preservatives, preservative enhancers, and actives in addition to the primary actives), provided that such optional components are physically and chemically compatible with the essential components described herein, and do not unduly impair stability, efficacy or other use benefits associated with the compositions of the present invention. Any optional ingredients should be compatible with the dehydroacetic acid such that its activity does not decrease unacceptably, preferably not to any significant extent, over a useful period (preferably at least about six months under normal storage conditions). Optional components may be dispersed, dissolved or the like in the carrier of the present compositions.

The compositions of the subject invention may optionally comprise other actives capable of functioning in different ways to enhance the benefits of the dehydroacetic acid and the ancillary actives and/or to provide other benefits. Optional components include aesthetic agents and other active agents. For example, the compositions may include absorbents, abrasives, anticaking agents, antifoaming agents, antimicrobial agents, binders, biological additives, buffering agents, bulking agents, chemical additives, cosmetic biocides, denaturants, cosmetic astringents, drug astringents, external analgesics, film formers, humectants, opaciiying agents, fragrances, pigments, colorings, essential oils, skin sensates, emollients, skin soothing agents, skin healing agents, pH adjusters, plasticizers, preservatives, preservative enhancers, propellants, reducing agents, additional skin-conditioning agents, skin penetration enhancing agents, skin protectants, solvents, suspending agents, emulsifiers, thickening agents, solubilizing agents, sunscreens, sunblocks, ultraviolet light absorbers or scattering agents, sunless tanning agents, antioxidants and/or radical scavengers, chelating agents, sequestrants, anti-acne agents, anti-inflammatory agents, anti-androgens, depilation agents, desquamation agents/exfoliants, organic hydroxy acids, vitamins and derivatives thereof, and natural extracts. Such other materials are known in the art. Nonexclusive examples of such materials are described in *Harry's Cosmeticology*, 7th Ed., Harry & Wilkinson (Hill Publishers, London 1982); in *Pharmaceutical Dosage Forms-Disperse Systems*; Lieberman, Rieger & Banker, Vols. 1 (1988) & 2 (1989); Marcel Decker, Inc.; in *The Chemistry and Manufacture of Cosmetics* 2nd. Ed., deNavarre (Van Nostrand 1962–1965); and in *The Handbook of Cosmetic Science and Technology*, 1st Ed. Knowlton & Pearce (Elsevier 1993).

Specific examples of optional components include the following. The active ingredients useful herein are categorized by their cosmetic and/or therapeutic benefit or their postulated mode of action. However, it is to be understood that the active ingredients useful herein can in some instances provide more than one cosmetic and/or therapeutic benefit or operate via more than one mode of action. Therefore, classifications herein are made for the sake of convenience and are not intended to limit the active ingredient to that particular application or applications listed.

A. Sunscreens and Sunblocks

Exposure to ultraviolet light can result in significant skin damage, as well as, excessive scaling and texture changes of the stratum corneum. Therefore, the compositions of the subject invention preferably contain a sunscreen or sunblock. Suitable sunscreens or sunblocks may be organic or inorganic.

A wide variety of conventional sunscreening agents are suitable for use herein. Sagarin, et al., at Chapter VIII, pages 189 et seq., of *Cosmetics Science and Technology* (1972), discloses numerous suitable agents, and is incorporated herein by reference. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-propyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylacetoumbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one) and 4-isopropyl-di-benzoylmethane.

Of these, 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and mixtures of these compounds, are preferred.

More preferred organic sunscreens useful in the compositions useful in the subject invention are 2-ethylhexyl-p-methoxycinnamate, butylmethoxydibenzoyl-methane, 2-hydroxy-4-methoxybenzo-phenone, 2-phenylbenzimidazole-5-sulfonic acid, octyldirnethyl-p-aminobenzoicacid, octocrylene and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4- hydroxydibenzoylm ethane; 4-N,N-( 2-ethylhexyl) methyl-aminobenzoic acid ester of 2- hydroxy-4-(2-hydroxyethoxy)benzophenone; 4-N,N-(2-ethylhexyl)-methylaminobenzoic acid ester of 4-(2-hydroxyethoxy) dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

Suitable inorganic sunscreens or sunblocks include metal oxides, e.g., zinc oxide and titanium dioxide. For example, the use of a titanium dioxide in topical sunscreen compositions that is applicable to the present invention is described in copending application Ser. No. 08/448,942, filed on May 24, 1995, in the names of Jiang Yue, Lisa R. Dew and Donald L. Bissett, incorporated herein by reference.

Especially preferred sunscreens or sunblocks include the metal oxides such as zinc oxide and titanium dioxide, butylmethoxydibenzoylmethane, 2-ethylhexyl-p-methoxycinnamate, phenyl benzimidazole sulfonic acid, and octocrylene.

A safe and effective amount of the sunscreen or sunblock is used, typically from about 1% to about 20%, more typically from about 2% to about 10%. Exact amounts will vary depending upon the sunscreen chosen and the desired Sun Protection Factor (SPF).

An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

B. Anti-Oxidants/Radical Scavengers

Preferred compositions of the subject invention include an anti-oxidant/radical scavenger as an active in addition to the primary active agents. The anti-oxidant/radical scavenger is especially useful for providing protection against UV radiation which can cause increased scaling or texture changes in the stratum corneum and against other environmental agents which can cause skin damage. In addition, anti-oxidants are useful to reduce inflammation associated with acne, as discussed hereinbefore.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate), tocopherol (vitamin E), tocopherol sorbate, other esters of tocopherol (e.g., acetate, succinate, linoleate), butylated hydroxy benzoic acids and their salts, 6-hydroxy-2,5,7,8-tetramethylchroman-2-carboxylic acid (commercially available under the tradename Trolox$^R$), gallic acid and its alkyl esters, especially propyl gallate, uric acid and its salts and alkyl esters, sorbic acid and its salts, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, lysine, methionine, proline, superoxide dismutase, silymarin, tea extracts (e.g, green tea extracts), grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chattedjee, incorporated herein by reference.

C. Chelators

As used herein, "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995; all incorporated herein by reference. Preferred chelators useful in compositions of the subject invention are furildioxime and derivatives thereof.

D. Organic Hydroxy Acids and Keto Acids

Compositions of the present invention preferably comprise an organic hydroxy acid and/or a keto acid for providing benefits in regulating skin condition, especially in therapeutically regulating signs of skin aging, more especially wrinkles, fine lines, and pores. Suitable hydroxy acids include $C_1$–$C_{18}$ hydroxy acids, preferably $C_8$ or below. The hydroxy acids can be substituted or unsubstituted, straight chain, branched chain or cyclic (preferably straight chain), and saturated or unsaturated (mono- or poly-unsaturated) (preferably saturated). Non-limiting examples of suitable hydroxy acids include glycolic acid, lactic acid, salicylic acid, 5 octanoyl salicylic acid, hydroxyoctanoic acid, hydroxycaprylic acid, and lanolin fatty acids. A nonlimiting example of a keto acid is pyruvic acid. Preferred concentrations of the organic hydroxy and/or keto acid range from about 0.1% to about 10%, more preferably from about 0.2% to about 5%, also preferably from about 0.5% to about 2%. Lactic acid, salicylic acid, and pyruvic acid are preferred. The organic hydroxy acids enhance the skin appearance benefits of the present invention. For example, the organic hydroxy acids tend to improve the texture of the skin.

E. Desquamation Agents/Exfoliants

A safe and effective amount of a desquamation agent is preferably added to the compositions of the subject invention, more preferably from about 0.1% to about 10%, even more preferably from about 0.2% to about 5%, also preferably from about 0.5% to about 4% of the composition. Desquamation agents enhance the skin appearance benefits of the present invention. For example, the desquamation agents tend to improve the texture of the skin (e.g., smoothness). A variety of desquamation agents are known in the art and are suitable for use herein, including but not limited to the organic hydroxy agents described above. One desquamation system that is suitable for use herein comprises sulfhydryl compounds and zwitterionic surfactants and is described in copending application Ser. No. 08/480,632, filed on Jun. 7, 1995 in the name of Donald L. Bissett, corresponding to PCT application Ser. No. 95/08136, filed Jun. 29, 1995, each incorporated herein by reference. Another desquamation system that is suitable for use herein comprises salicylic acid and zwitterionic surfactants and is described in copending patent application Ser. No. 08/554,944, filed on Nov. 13, 1995 as a continuation of Ser. No. 08/209,401, filed on Mar. 9, 1994 in the name of Bissett, corresponding to PCT application Ser. No. 94/12745, filed Nov. 4, 1994, published May 18, 1995, each incorporated herein by reference. Zwitterionic surfactants such as described in these applications are also useful as desquamatory agents herein, with cetyl betaine being particularly preferred.

F. Depilation Agents

The compositions of the present invention may include a safe and effective amount of a depilation agent. When used, the composition preferably contains from about 0.1% to about 10%, more preferably from about 0.2% to about 5%, also preferably from about 0.5% to about 2% of depilation agent. A depilation agent preferred for use herein comprises a sulfhydryl compound, e.g., N-acetyl-L-cysteine. The use of such depilation agents is described in more detail in copending application Ser. No. 08/479,878, filed on Jun. 7, 1995, in the name of Greg G. Hillebrand and Vladimir Gartstein, corresponding to PCT application Ser. No. 95/07311, filed Jun. 8, 1995, each incorporated herein by reference.

G. Skin Lightening Agents

The compositions of the present invention may comprise a skin lightening agent. When used, the compositions preferably comprise from about 0.1% to about 10%, more preferably from about 0.2% to about 5%, also preferably from about 0.5% to about 2%, of a skin lightening agent Suitable skin lightening agents include those known in the art, including kojic acid, arbutin, niacinamide, ascorbic acid and derivatives thereof, e.g., magnesium ascorbyl phosphate. Skin lightening agents suitable for use herein also include those described in copending patent application Ser. No. 08/479,935, filed on Jun. 7, 1995 in the name of Hillebrand, corresponding to PCT application Ser. No. 95/07432, filed Jun. 12, 1995; and copending patent application Ser. No. 08/390,152, filed on Feb. 24, 1995 in the names of Kalla L. Kvalnes, Mitchell A. DeLong, Barton J. Bradbury, Curtis B. Motley, and John D. Carter, corresponding to PCT application Ser. No. 95/02809, filed Mar. 1, 1995, published Sep. 8, 1995; all incorporated herein by reference.

H. Zinc Salts

When a vitamin $B_3$ compound is included the present composition, the compositions of the present invention may further comprise a zinc salt. Zinc salts are especially preferred where the composition contains a sulfhydryl compound, e.g., N-acetyl-L-cysteine. Without intending to be limited or bound by theory, it is believed that the zinc salt acts as a chelating agent capable of complexing with the sulfhydryl compound prior to topical application, stabilizes the sulfhydryl compound and/or controls odor associated with the sulfhydryl compound. Concentrations of the zinc salt can range from about 0.001% to about 10%, more preferably from about 0.01% to about 5%, most preferably from about 0.1% to about 0.5% by weight of the composition.

Preferred zinc salts include zinc acetate, zinc acetate hydrates such as zinc acetate-2-water, zinc aluminum oxide complexes such as gahnite, zinc diamine, zinc antimonide, zinc bromate hydrates such as zinc bromate-6-water, zinc bromide, zinc carbonates such as zincspar and smithsonite, zinc chlorate hydrates such as zinc chlorate-4-water, zinc chloride, zinc diamine dichloride, zinc citrate, zinc chromate, zinc dichromate, zinc diphosphate, zinc hexacyanofluoride ferrate (II), zinc fluoride, zinc fluoride hydrates such as zinc fluoride-4-water, zinc formate, zinc formate hydrates such as zinc formate-2-water, zinc hydroxide, zinc iodate, zinc iodate hydrates such as zinc iodate-2-water, zinc iodide, zinc iron oxide complexes, zinc nitrate hydrates such as zinc nitrate-6-water, zinc nitride, zinc oxalate hydrates such as zinc oxalate-2-water, zinc oxides such as zincite, zinc perchlorate hydrates such as zinc perchlorate-6-water, zinc permanganate hydrates such as zinc permanganate-6-water, zinc peroxide, zinc p-phenolsulfonate hydrates such as zinc p-phenosulfonate-8-water, zinc phosphate, zinc phosphate hydrates such as zinc phosphate-4-water, zinc phosphide, zinc propionate, zinc selenate hydrates such as zinc selenate-5-water, zinc selenide, zinc silicates such as zinc silicate (2) and zinc silicate (4), zinc silicon oxide water complexes such as hemitnorphite, zinc hexafluorosilicate hydrates such as zinc hexafluorosilicate-6-water, zinc stearate, zinc sulfate, zinc sulfate hydrates such as zinc sulfate-7-water, zinc sulfide, zinc sulfite hydrates such as zinc sulfite-2-water, zinc telluride, zinc thiocyanate, zinc (II) salts of N-acetyl L-cysteine, and mixtures thereof.

Especially preferred zinc salts include zinc citrate, zinc oxide, zinc chloride, zinc acetate, zinc stearate, zinc sulfate, and mixtures thereof. Zinc citrate is especially preferred.

I. Humectants, Moisturizers, and Skin Conditioners

The compositions of the present invention may further comprise a humectant, moisturizing agent or other skin conditioning agent. A variety of these materials can be employed and each can be present at a level of from or about 0.1% to or about 20%, more preferably from or about 1% to or about 10%, and most preferably from or about 2% to or about 5%. These materials include guanidine (e.g., urea guanidine betaine); glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof.

Also useful herein are the propoxylated glycerols described in U.S. Pat. No. 4,976,953, which is description is incorporated herein by reference.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

J. Other Optional Components

The compositions of the present invention may also include an extract obtained by suitable physical and/or chemical isolation from natural sources (e.g., plants, fungi, by-products of microorganisms), including those known in the topical personal care art. Preferred extracts are those which enhance the skin appearance benefits of the present invention, and which are preferably used in a safe and effective amount, more preferably an amount of from 0.1% to about 20%, even more preferably 0.5% to about 10%, also from 1% to about 5%. Such extracts include plant and fungal extracts such as extracts of yeast, rice bran, and of the plant *Centella Asiatica*. Natural extracts of *Centella Asiatica* are preferred and are commercially available from MMP, Inc. of Plainfield, N.J. under the trade name(s) Centella Asiatica E.P.C.A. ("Extract Purified of *Centella asiatica*") and *Genines amel*. *Genines amel* is the purer form of the extract.

Compounds which are known to stimulate the production of collagen can also be used in the present invention. Such compounds include Factor X (kinetin), Factor Z (zeatin), n-methyl taurine, dipalmitoyl hydroxyproline, palmitoyl hydroxy wheat protein, biopeptide CL (palmitoyl glycyl-histidyl-lysine), ASC III (Amplifier of Synthesis of Collagen III, E. Merck, Germany), and beta glucan.

The compositions hereof can also include natural ceramides or the like, for example, ceramide 1- 6.

Other examples of additional components useful herein include the following: water-soluble vitamins and derivatives thereof [e.g., vitamin C]; polyethyleneglycols and polypropyleneglycols; polymers for aiding the film-forming properties and substantivity of the composition (such as a copolymer of eicosene and vinyl pyrrolidone, an example of which is available from GAF Chemical Corporation as Ganex® V-220). Also useful are crosslinked and non-crosslinked nonionic and cationic polyacrylamides [e.g., Salcare SC92 which has the CTFA designation polyquaternium 32 (and) mineral oil, and Salcare SC 95 which has the CTFA designation polyquatemium 37 (and) mineral oil (and) PPG-1 trideceth-6, and the nonionic Seppi-Gel polyacrylamides available from Seppic Corp.]. Also useful are crosslinked and uncrosslinked carboxylic acid polymers and copolymers such as those containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (examples useful herein include the carbomers, which are homopolymers of acrylic acid crosslinked with allyl ethers of sucrose or pentaerytritol and which are available as the Carbopol® 900 series from B.F. Goodrich, and copolymers of $C_{10\text{-}30}$ alkyl acrylates with one or more monomers of acrylic acid, methacrylic acid, or one of their short chain (i.e., $C_{1\text{-}4}$ alcohol) esters, wherein the crosslinking agent is an allyl ether of sucrose or pentaerytritol, these copolymers being known as acrylates/C10–30 alkyl acrylate crosspolymers and are commercially available as Carbopol® 1342, Pemulen TR-1, and Pemulen TR-2, from B.F. Goodrich). These carboxylic acid polymers and copolymers are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which are incorporated by reference herein. See also *CTFA International Cosmetic Ingredient Dictionary*, fourth edition, 1991, pp. 12 and 80; which is also incorporated herein by reference.

Also useful herein are aesthetic components such as fragrances, pigments, colorings, essential oils, skin sensates, astringents, skin soothing agents, skin healing agents and the like, nonlimiting examples of these aesthetic components include clove oil, menthol, camphor, eucalyptus oil, eugenol, menthyl lactate, witch hazel distillate, bisabolol, dipotassium glycyrrhizinate and the like.

Preparation of Compositions

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like.

Methods For Reducing Sebum Synthesis and Regulating the Oily/Shiny Appearance of Skin The subject invention relates to methods of reducing sebum synthesis and regulating the oily and/or shiny appearance of skin. Such methods comprise topically applying to the skin to be treated an effective amount of the compositions of the subject invention so as to deposit an effective amount of primary active on the skin. The term "effective amount", as used herein, means an amount sufficient to reduce sebum synthesis and regulate oily and/or shiny appearance of skin as defined herein. In general, a safe and effective amount of the primary actives are left in contact with the skin for a period sufficient to provide noticeable effects, generally after chronic application such as described herein.

The composition can be applied for several days, weeks, months or years at appropriate intervals. The compositions are preferably applied from about four times a day to about once every three days, more preferably from about twice a day to once every other day, also about once a day, until a satisfactory reduction in sebum synthesis or oily and/or shiny skin appearance improvement has been achieved. The reduction in sebum synthesis and the regulation of the appearance of oily and/or shiny skin can be observed visually without magnification. Methods of quantifying reduction in sebum synthesis and the regulation of the appearance of oily and/or shiny skin such as are known in the art can also be employed, e.g., sebutape analysis such as known in the art.

Typically, in each application, an effective coating of the skin with primary active is achieved by topically applying (in terms of mg active/cm$^2$ skin) from about 0.0002 mg/cm$^2$ to about 0.5 mg/cm$^2$ of primary active to the skin to be treated. More preferably, from about 0.002 mg/cm$^2$ to about 0.2 mg/cm$^2$ of primary active is applied. Most preferably, from about 0.02 mg/cm$^2$ to about 0.1 mg/cm$^2$ of primary active is applied. The amount of composition that is applied may be, for example, from about 0.01 mg to about 5 mg composition/cm$^2$ skin, preferably about 1 to about 2 mg composition/cm$^2$ skin.

The compositions are generally applied by lightly massaging the composition into the skin, typically in the amounts described above.

The compositions of the invention can also be used for reducing sebum synthesis and regulating oiliness of the scalp and for controlling dandruff. Methods of regulating scalp oiliness and for controlling dandruff are as described above, wherein the composition is applied to the scalp.

EXAMPLES

The following examples further describe and demonstrate embodiments within the scope of the subject invention. The examples are given solely for the purpose of illustration and are not to be construed as limitations of the subject invention, as many variations thereof are possible without departing from the spirit and scope of the invention.

Example 1

A skin gel is prepared by conventional methods from the following components.

|  | Ingredient (CTFA Name) | Weight % |
|---|---|---|
| PHASE A: | Water | 10.00 |
|  | Sodium Dehydroacetate | 2.00 |
| PHASE B: | Water | 84.03 |
|  | Carbomer | 0.65 |
|  | Disodium EDTA | 0.10 |
|  | Methylparaben | 0.20 |
| PHASE C: | Glycerin | 2.00 |
| PHASE D: | Sodium Hydroxide | 0.52 |
| PHASE E: | Phenoxyethanol | 0.50 |

Blend the Phase A components with a suitable mixer until dissolved. Separately, blend the Phase B components with a suitable mixer and heat to 70° C. with mixing to melt the components. Add the Phase C components to Phase B and mix until dispersed. Begin to cool the batch, then add the D Phase. Once Phase D is dispersed, add Phase A to the batch and continue cooling and mixing. When the batch reaches 40° C. add the Phase E component and stir until completely dispersed.

Apply the composition to a subject's facial acne or oily/shiny skin at 2 mg composition/cm$^2$ skin once or twice daily for a period of from 2 weeks to 6 months to reduce facial oiliness and acne.

Example 2

The following lotions are prepared by mixing the ingredients in each composition according to conventional mixing techniques well known to those skilled in the art of formulating skin care compositions.

| Ingredient | Composition 1 (% Weight) | Composition 2 (% Weight) | Composition 3 (% Weight) |
|---|---|---|---|
| Salicylic acid | 0.5 | 2.0 | 2.0 |
| Absolute ethanol | 40.0 | 40.0 | 40.0 |
| Propylene Glycol | 25.0 | 25.0 | 25.0 |
| Dehydroacetic acid | 2.0 | 2.0 | 1.0 |
| Perfume | 0.2 | 0.2 | 0.2 |
| Water | q.s | q.s | q.s |

Any of the above compositions is applied to the face at a dose of 0.2 ml, up to four times a day to treat oily/shiny skin or existing acne.

Example 3

A skin cream is prepared by conventional methods from the following components.

|  | Ingredient (CTFA Name) | Weight % |
|---|---|---|
| PHASE A: | Water U.S.P. | 57.31 |
|  | Disodium EDTA | 0.13 |
|  | Methyl Paraben | 0.25 |
|  | Glycerin | 3.00 |
|  | Zinc Citrate | 1.00 |
| PHASE B: | Cetyl Alcohol | 0.56 |
|  | Stearyl Alcohol | 2.03 |
|  | Behenyl Alcohol | 0.22 |
|  | Steareth-21 (Brij 721) | 0.37 |
|  | Steareth-2 (Brij 72) | 1.10 |
|  | Distearyldimonium chloride (Varisoft TA-100) | 0.95 |
|  | Propyl Paraben | 0.10 |
|  | Polypropylene glycol-15 stearyl ether (Arlamol E) | 3.25 |
| PHASE C: | Polypropylene glycol-15 stearyl ether (Arlamol E) | 2.17 |
|  | titanium dioxide | 0.75 |
| PHASE D: | Sodium Dehydroacetate | 5.00 |
|  | Citric acid | 0.19 |
|  | water U.S.P. | 17.00 |
|  | 50% NaOH | 0.94 |
| PHASE E: | Benzyl Alcohol | 0.50 |
|  | Silicone fluid (DC Q2 - 1401; cyclomethicone/dimethiconol - 50/50 blend | 0.75 |
|  | dimethicone 10 cst | 1.00 |
|  | polyethylene Low Density Beads | 1.00 |
| PHASE F: | Fragrance | 0.10 |
| PHASE G: | 50% NaOH | 0.33 |

Blend the A phase components with a suitable mixer (e.g., Tekmar model RW20DZM), heating while stirring to a temperature of 70–80° C. Separately, blend the B phase components with a suitable mixer and heat with mixing to melt the components. Separately, blend the C phase components and mill to obtain an acceptably smooth mixture (e.g., using a Tekmar T50 Mill).

Add the C phase mixture to the B phase mixture and mix. Then add the resulting mix to the A phase mixture with mixing, cool with a cold water bath and mill, then continue stirring. Remove the combination from the bath, with continued stirring, once the temperature reaches 40° C.

Separately, blend the D phase components by stirring until dissolved, then add this to the combination of A–C materials.

Separately, blend the E phase components by mixing until smooth and continuous, then add this to the combination of the A–D materials. Add and mix the fragrance, then the NaOH. Adjust the pH as necessary to 5.5.

Apply the composition to a subject's facial acne or oily/shiny skin at 2 mg composition/cm$^2$ skin once or twice daily for a period of from 2 weeks to 6 months to reduce facial oiliness and acne.

Example 4

An emulsion is prepared by conventional methods from the following components:

| Ingredient | Weight % |
|---|---|
| Silicone fluid (Dow Corning DC 345) | 15.0 |
| Silicone fluid (Dow Corning DC 3225C) | 2.5 |
| Silicone fluid (Goldschmidt Abil We09) | 2.5 |
| Water | 71.4 |
| Sodium Dehydroacetate | 5.0 |
| Tetrasodium EDTA | 0.1 |
| Benzyl alcohol | 0.3 |
| Methyl paraben | 0.2 |
| Glycerin | 3.0 |

Form the water phase in a suitable vessel charged with the water as follows: add the glycerin and then niacinamide to the water with stirring. Add to this mixture with stirring the methyl paraben dissolved in the benzyl alcohol. Add to this mixture with stirring the EDTA.

Form the silicone phase in a separate suitable vessel by adding and stirring together the silicone fluids.

Add the water phase to the silicone phase slowly with stirring to form the emulsion.

Apply the composition to a subject's facial acne or oily skin at 2 mg composition/cm$^2$ skin once or twice daily for a period of from 2 weeks to 6 months to reduce facial oiliness and acne.

Example 5

A skin cream is prepared by conventional methods from the following components.

| | Ingredient (CTFA Name) | Weight % |
|---|---|---|
| PHASE A: | Water U.S.P. | 63.96 |
| | Disodium EDTA | 0.15 |
| | Glycerin | 5 |
| PHASE B: | Cetyl hydroxy ethyl cellulose | 0.15 |
| | Methyl Paraben | 0.25 |
| PHASE C: | Cetyl Alcohol | 0.5 |
| | Stearyl Alcohol | 0.5 |
| | Behenyl Alcohol | 0.5 |
| | Cetyl ricinoleate | 3 |
| | Steareth-2 (Brij 72) | 1.05 |
| | Distearyldimonium chloride (Varisoft TA-100) | 0.25 |
| | Propyl Paraben | 0.10 |
| | Myristyl myristate | 1.5 |
| | Caprylic/Capritryglycerides | 1.5 |
| | Mineral oil | 2 |
| | Fatty acid ester of sugar* | 1 |
| | Polypropylene glycol-15 stearyl ether (Arlamol E) | 1.05 |
| PHASE D: | dimethicone 10 cst (Dow Corning) | 2 |
| PHASE E: | Sodium dehydroacetate | 5 |
| | Water U.S.P. | 10 |
| PHASE F: | Benzyl Alcohol | 0.5 |
| PHASE 6: | 50% NaOH | 0.04 |

*A C1–C30 monoester or polyester of sugars and one or more carboxylic acid moieties as described herein, preferably a sucrose polyester in which the degree of esterification is 7–8, and in which the fatty acid moieties are C18 mono- and/or di-unsaturated and behenic, in a molar ratio of unsaturates:behenic of 1:7 to 3:5, more preferably the octaester of sucrose in which thereare about 7 behenic fatty acid moieties and about 1 oleic acid moiety in the molecule, e.g., sucrose ester of cottonseed oil fatty acids.

Blend the A phase components with a suitable mixer (e.g., Tekmar model RW20DZM), heating while stirring to a temperature of about 70–80° C. Add the cetyl hyroxy ethyl cellulose and methyl paraben with mixing at about 70–80° C. to melt the components. Separately, blend the C phase components and mill to obtain an acceptably smooth mixture (e.g., using a Tekmar T50 Mill).

Add the C phase mixture to the above mixture and mix. Remove the combination from the bath, with continued stirring, once the temperature reaches about 45° C. Add the dimethicone and mix.

Separately, blend the E phase components by mixing until smooth and continuous, then add this to the above mixture. Add and mix in the benzyl alcohol, then the NaOH. Adjust the pH as necessary to 7.

Apply the composition to a subject's facial acne or oily skin at 2 mg composition/cm$^2$ skin once or twice daily for a period of from 2 weeks to 6 months to reduce facial oiliness and acne.

Example 6

A skin cream is prepared by conventional methods from the following components.

| | Component | Weight % |
|---|---|---|
| PHASE A: | benzyl alcohol | 0.30 |
| | methyl p-hydroxybenzoate (a.k.a. methyl-paraben) | 0.20 |
| | ethanol | 3.00 |
| PHASE B: | water | 60.60–61.35 |
| | disodium EDTA | 0.50 |
| | glycerol | 10.00 |
| | hexylene glycol | 2.00 |
| | Sodium Dehydroacetate | 2.00 |
| | triethanol amine | 0.05 |
| | butylated hydroxytoluene | 0.10 |
| PHASE C: | Dow Corning 345 Fluid | 12.50 |
| | Abil WE-09 | 2.50 |
| | Dow Corning-3225C | 2.50 |
| | petrolatum | 1.50 |
| | retinol (10% in soybean oil) | 0.75–1.50 |
| | fatty acid ester of sugar* | 1.00 |

*See Example 5

Blend the A phase components with a suitable mixer (e.g., Tekmar model RW20DZM). Blend the B phase components into the A phase with a suitable mixer. Separately, blend the C phase components until they are uniform. Add the C phase mixture to the A/B phase mixture, mix until uniform and emulsified, and then mill to obtain an acceptably smooth mixture (e.g., using a Tekmar T50 Mill).

Apply the composition to a subject's facial acne or oily skin at 2 mg composition/cm$^2$ skin once or twice daily for a period of from 2 weeks to 6 months to reduce facial oiliness and acne.

Example 7

A bath oil having the composition A, B or C is prepared by combining the following components using conventional mixing and formulating techniques well known to those skilled in the art of skin care formulations.

| | A (wt %) | B (wt %) | C (wt %) |
|---|---|---|---|
| POE 20 sorbitan monopalmitate | — | 5 | 22.2 |
| Fragrance oil | 35 | 5 | 4.4 |
| Isopropyl Myristate | 65 | — | — |

-continued

|  | A (wt %) | B (wt %) | C (wt %) |
|---|---|---|---|
| Methyl p-Hydroxybenzoate | — | 0.18 | — |
| Propyl p-Hydroxybenzoate | — | 0.02 | — |
| Sodium Lauryl Sulfate | — | — | 10 |
| Ninol AA-63 | — | — | 1 |
| Sorbic acid | — | — | 0.2 |
| Sodium Dehydroacetate | 4 | 4 | 4 |
| water q.s. | — | 100 | 100 |

Apply the bath oil to the skin either as prepared or in aqueous diluted form. Apply in a dose of from 1–2 mg oil /cm$^2$ skin for four weeks, to observe a decrease in skin oil and/or shine.

Example 8

A hair conditioner is prepared by combining the following components using conventional mixing and formulating techniques well known to those skilled in the art of skin care formulations.

|  | wt % |
|---|---|
| PVP K-30 (polymeric dispersing agent) | 3 |
| Neobee M-20 (propylene glycol dicaprylate) | 5 |
| Drewmulse 1128 (surfactant) | 5 |
| water | 69.5 |
| triethanolamine | 1 |
| carbopol 934 (carbomer, polymeric thickening/dispersing agent) | 1 |
| WSP-X250 | 5 |
| Amerchol L-101(mineral oil/lanolin oil) | 3 |
| Lipal 15 CSA | 3 |
| preservative | q.s. |
| perfume | 0.5 |
| Sodium Dehydroacetate | 4 |

Apply the conditioner to the scalp, preferably to clean hair, every other day to once a day to reduce the appearance of oily hair and the occurrence of dandruff. Apply a dose of about 0.5 ml and wash off.

Example 9

A liquid shampoo having the composition A, B or C is prepared by combining the following components using conventional mixing and formulating techniques well known to those skilled in the art of skin care formulations.

|  | A (wt %) | B (wt %) | C (wt %) |
|---|---|---|---|
| coconut oil | 14 | 18 | — |
| olive oil | 3 | — | — |
| castor oil | 3 | 4 | — |
| potassium hydroxide, 85% | 4.7 | 5.3 | — |
| glycerol | 2 | 4 | 5 |
| ethyl alcohol | 4 | — | 10 |
| sodium hexametaphosphate | 1 | — | — |
| perfume | 0.3 | 0.2 | q.s. |
| water | 64 | 64 | 36 |
| borax | — | 0.5 | — |
| coconut soap potassium salt | — | — | 35 |
| olive oil soft soap | — | — | 10 |
| Sodium Dehydroacetate | 4 | 4 | 4 |

Apply the shampoo to the scalp every other day to once a day to reduce the appearance of oily hair and the occurrence of dandruff. A dose of about 0.5 ml is applied and washed off.

Example 10

A topical composition suitable for use as a liquid make-up foundation is prepared from the following ingredients using conventional mixing and formulating techniques well known to those skilled in the art of skin care formulations.

|  | wt % |
|---|---|
| dimethicone copolyol/cyclomethicone (Dow Corning QZ-3225C) | 10 |
| cyclomethicone (Dow Corning 344 fluid) | 17.74 |
| pigments | 3.7 |
| titanium dioxide | 8.25 |
| trihydroxy stearin | 0.3 |
| aqueous floral extract | 0.01 |
| denatured ethanol | 4–17 |
| salicylic acid | 1.45 |
| dipropylene glycol | 0–14 |
| PVP (polymeric dispersing agent) | 1 |
| procetyl AWS (PPG-5 ceteteth, surfactant) | 3 |
| tri-sodium citrate | 0.3 |
| tetrasodium EDTA | 0.1 |
| glycerin | 10–30 |
| Dehydroacetic acid | 4 |
| sodium chloride | 0.3 |
| water | 15.85–34.85 |

Apply the composition to a person's face once per day in an amount of 1–2 mg composition/cm$^2$ skin for four weeks, to observe a decrease in facial oil and/or shine, a reduction in oily breakthrough, longer wear of the composition, and more even coverage as time passes.

Example 11

A water-in-oil topical composition suitable for use as a liquid make-up foundation is prepared from the following ingredients using conventional mixing and formulating techniques such described below.

| Compounding code | Ingredient | Wt. % |
|---|---|---|
| A | cyclomethicone | 9.25 |
| A | cetyl octanoate | 2.00 |
| A | dimethicone copolyol (DC3225C) | 20.00 |
| B | talc | 3.38 |
| B | pigment | 10.51 |
| B | Spheron L-1500 | 0.50 |
| C | Synthetic Wax Durachem 0602 | 0.10 |
| C | Arachidyl behenate | 0.30 |
| D | cyclomethicone | 1.00 |
| D | trihydroxystearin | 0.30 |
| E | laureth-7 | 0.50 |
| E | propyl paraben | 0.25 |
| F | fragrance | 0.05 |
| G | water | 34.44 |
| G | methyl paraben | 0.12 |
| G | propylene glycol | 8.00 |
| G | Sodium Dehyroacetate | 4.00 |
| G | glycerin | 3.00 |
| G | sodium chloride | 2.00 |
| G | sodium dehydroacetate | 0.30 |

Combine the ingredients A and B in a suitable container. Mix the ingredients using a Silverson L4RT mixer equipped w/a 1" tubular assembly and a square hole screen for 30 minutes at 9000 rpm (the container can be covered to avoid loss of any volatile or other materials). Heat the resultant mixture to 85–90° C. Add ingredients C, mix for 5 minutes at 2100 rpm using a Silverson L4RT mixer w/a 2" head and a disintegrating screen. The container should be covered to minimize evaporation of cyclomethicone and other volatile or nonvolatile materials. Cool the resultant mixture to 45–55° C.

Combine the ingredients D components and mix until a uniform slurry is formed. Separately, combine the ingredients E and mix until a uniform slurry is formed. Add the resultant slurries to the mixture of A, B and C (which is at 45–55° C), mix for 5 minutes at 2100 rpm using a Silverson L4RT equipped w/a 2" head and a disintegrating screen. Cool the resultant mixture to 30° C, then add ingredient F. Mix 5 minutes at 2100 rpm using a Silverson L4RT equipped w/a 2" head and a disintegrating screen.

Combine the ingredients G in a suitable container and mix until all components are dissolved. Slowly add the resultant solution to the mixture of A–F. Emulsify this combination using a Silverson L4RT mixer equipped w/a 2" head and a disintegrating screen at 2100–5100 rpm (rpms will increase as the mixture thickens), continue mixing for 5 minutes after all of the G mixture is added.

Apply the composition to a person's face once per day in an amount of 1–2 mg composition/cm$^2$ skin for four weeks, to observe a decrease in facial oil, a reduction in oily breakthrough, longer wear of the foundation, and more even coverage as the time period passes.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed is:

1. A method of inhibiting sebaceous gland activity in mammalian skin and scalp, which method comprises the step of administering to the skin or scalp of a mammal susceptible to having excessive sebaceous gland activity a topical composition consisting essentially of:
   (a) a safe and effective amount of dehydroacetic acid or pharmaceutically-acceptable salts thereof, and
   (b) a dennatologically-acceptable carrier.

2. A method of treating acne in mammalian skin, which method comprises the step of administering to a mammal susceptible to or having acne a topical composition consisting essentially of:
   (a) a safe and effective amount of dehydroacetic acid or pharmaceutically-acceptable salts thereof, and
   (b) a dermatologically-acceptable carrier.

3. A method of regulating skin condition in mammalian skin, which method comprises the step of administering to a mammal having skin wrinkles, fine lines, or large pores, a topical composition consisting essentially of:
   (a) a safe and effective amount of dehydroacetic acid or pharmaceutically-acceptable salts thereof;
   (b) a dermatologically-acceptable carrier.

* * * * *

UNITED STATES PATENT AND TRADEMARK OFFICE
CERTIFICATE OF CORRECTION

PATENT NO. : 6,150,403
DATED : November 21, 2000
INVENTOR(S) : K. A. Biedermann et al.

Page 1 of 2

It is certified that error appears in the above-identified patent and that said Letters Patent is hereby corrected as shown below:

Title page,
Under OTHER PUBLICATIONS, insert

-- McCarthy, T.J., "Effect of pH on Stored Dehydroacetic Acid Solutions", Cosmetics and Perfumery, Vol. 89, pp. 45-48 (12/74). --

Column 7,
Line 38, "niacinanide" should read -- niacinamide --.

Column 10,
Line 62, "triarncinolone" should read -- triamcinolone --.

Column 11,
Line 53, "Comminhora" should read -- Commiphora --.

Column 12,
Line 14, "fmasteride" should read -- finasteride --.

Column 13,
Line 57, "aphase" should read -- phase --.

Column 19,
Line 48, "Deterents" should read -- Detergents --.

Column 23,
Line 67, "Technoloy" should read -- Technology --.

Column 24,
Line 3, "0.I%" should read -- 0.1% --.

Column 25,
Line 29, "opaciiying" should read -- opacifying --.

Column 26,
Lines 55 and 56, "octyldirnethyl-p-aminobenzoicacid" should read -- octyldimethyl-p-aminobenzoic acid --.

Column 28,
Line 11, "Chattedjee" should read -- Chatterjee --.

UNITED STATES PATENT AND TRADEMARK OFFICE
CERTIFICATE OF CORRECTION

PATENT NO. : 6,150,403 B1
DATED : Novemeber 21, 2001
INVENTOR(S) : K. A. Biedermann et al.

It is certified that error appears in the above-identified patent and that said Letters Patent is hereby corrected as shown below:

Column 29,
Line 35, "agent" should read -- agent. --.

Column 30,
Line 20, "hemitnorphite" should read -- hemimorphite --.

Column 38,
Line 37, "such described" should read -- such as described --.

Column 40,
Line 13, "dennatologically-acceptable" should read -- dermatologically-acceptable --.
Line 27, insert
-- (b) a compound selected from the group consisting or organic acids, retinoids, and mixtures thereof; and --.
Line 27, "(b)" should read -- (c) --.

Signed and Sealed this

Twenty-third Day of October, 2001

Attest:

NICHOLAS P. GODICI
Attesting Officer
Acting Director of the United States Patent and Trademark Office